United States Patent
Moser et al.

(10) Patent No.: US 11,925,644 B2
(45) Date of Patent: *Mar. 12, 2024

(54) CRYSTALLINE SALTS OF 5-METHYL-(6S)-TETRAHYDROFOLIC ACID AND L-LEUCINE ETHYL ESTER

(71) Applicant: MERCK PATENT GMBH, Darmstadt (DE)

(72) Inventors: Rudolf Moser, Schaffhausen (CH); Viola Groehn, Dachsen (CH); Ruth Boehni Stamm, Stein Am Rhein (CH); Fritz Blatter, Reinach (CH); Martin Szelagiewicz, Basel (CH)

(73) Assignee: MERCK PATENT GMBH, Darmstadt (DE)

( * ) Notice: Subject to any disclaimer, the term of this patent is extended or adjusted under 35 U.S.C. 154(b) by 344 days.

This patent is subject to a terminal disclaimer.

(21) Appl. No.: 17/258,086

(22) PCT Filed: Jul. 2, 2019

(86) PCT No.: PCT/EP2019/067698
§ 371 (c)(1),
(2) Date: Jan. 5, 2021

(87) PCT Pub. No.: WO2020/007839
PCT Pub. Date: Jan. 9, 2020

(65) Prior Publication Data
US 2021/0283136 A1    Sep. 16, 2021

(30) Foreign Application Priority Data
Jul. 6, 2018 (EP) .................................... 18182279

(51) Int. Cl.
A61K 31/519 (2006.01)
A61K 9/14 (2006.01)
A61K 47/14 (2017.01)
C07D 487/04 (2006.01)

(52) U.S. Cl.
CPC ............ *A61K 31/519* (2013.01); *A61K 9/145* (2013.01); *A61K 47/14* (2013.01); *C07D 487/04* (2013.01); *C07B 2200/13* (2013.01)

(58) Field of Classification Search
CPC ...... A61K 31/519; A61K 9/145; A61K 47/14; C07D 487/04; C07D 475/04; C07B 2200/13; A61P 7/00; A61P 9/00; A61P 19/10; A61P 25/00; A61P 25/28; C07C 229/08
USPC ......................................................... 514/249
See application file for complete search history.

(56) References Cited

U.S. PATENT DOCUMENTS

| 6,441,168 B1 * | 8/2002 | Muller | A61P 29/00 544/258 |
| 2016/0207925 A1 | 7/2016 | Fracchia | |

FOREIGN PATENT DOCUMENTS

| CN | 103664945 A | 3/2014 | |
| CN | 107304212 A | * 10/2017 | ........... C07D 475/04 |
| CN | 107304212 A | 10/2017 | |
| JP | S37-10698 B | 8/1962 | |

OTHER PUBLICATIONS

Office Action in corresponding Chinese Application for Invention No. 201980043620.4 dated Dec. 16, 2022 (pp. 1-8) and english translation therof (pp. 1-11).
International search report PCT/EP2019/067698 dated Sep. 13, 2019 (pp. 1-3).
English translation of Office Action in corresponding Japanese Patent Application: 2021-500074 Dispatched Jul. 4, 2023 (pp. 1-4).
English translation of JP S37-10698 dated Aug. 9, 1962 (pp. 1-2).

* cited by examiner

*Primary Examiner* — Jared Barsky
*Assistant Examiner* — Liyuan Mou
(74) *Attorney, Agent, or Firm* — MILLEN, WHITE, ZELANO & BRANIGAN, P.C.; Csaba Henter

(57) ABSTRACT

The present invention refers to a crystalline salt comprising 5-methyl-(6S)-tetrahydrofolic acid L-leucine ethyl ester wherein the molar ratio of 5-methyl-(6S)-tetrahydrofolic acid and L-leucine ethyl ester is from 1:0.3 to 1:3.0 (in mol/mol) and/or hydrates and/or solvates thereof as well as to a process of obtaining the same.

13 Claims, 2 Drawing Sheets

CRYSTALLINE SALTS OF 5-METHYL-(6S)-TETRAHYDROFOLIC ACID AND L-LEUCINE ETHYL ESTER

The present invention is directed to a crystalline salt comprising 5-methyl-(6S)-tetrahydrofolic acid and L-leucine ethyl ester wherein the molar ratio of 5-methyl-(6S)-tetrahydrofolic acid to L-leucine ethyl ester is from 1:0.3 to 1:3.0 (in mol/mol) and/or hydrates and/or solvates thereof.

Tetrahydrofolates are predominantly used as the calcium salt of 5-formyltetrahydrofolic acid (leucovorin and levoleucovorin), as the calcium salt of 5-methyltetrahydrofolic acid (Metafolin®), or as the sulfate salt of 5,10-methylenetetrahydrofolic acid (Modufolin®). Most prominent fields of use are for the treatment of megaloblastic folic acid anaemia, as an antidote for increasing the compatibility of folic acid antagonists, particularly of aminopterin and methotrexate in cancer therapy ("antifolate rescue"), for increasing the therapeutic effect of fluorinated pyrimidines and for the treatment of autoimmune diseases such as psoriasis and rheumatoid arthritis, for increasing the compatibility of certain antiparasitic for mutations, for instance trimethoprim-sulfamethoxazole, and for reducing the toxicity of dideazatetrahydrofolates in chemotherapy.

The calcium salt of 5-methyl-(6S)-tetrahydrofolic acid is used in particular as a drug and as a food additive, as a vitamin preparation, for the prevention of neural tube defects, for the treatment of depressive illnesses, and for influencing the homocysteine level.

5-Methyl-(6S)-tetrahydrofolic acid and salts thereof are known to be extremely unstable. In particular they are highly susceptible to oxidation [see also A. L. Fitzhugh, Pteridines 4 (4), 187-191 (1993) in this respect] and therefore difficult to produce at a level of purity which is acceptable for a pharmaceutical active ingredient or a food additive.

Various methods, such as excluding oxygen as completely as possible or the addition of antioxidants such as ascorbic acid or reduced L-glutathione, have been employed in order to overcome the instability of 5-methyltetrahydrofolic acid and salts thereof. U.S. Pat. No. 6,441,168 B1 discloses alkaline earth metal salts of 5-methyltetrahydrofolic acid, particularly the calcium salt, its crystallization and its use. The drawback of such crystalline calcium salt of 5-methyl-(6S)-tetrahydrofolic acid is that it exists in its crystalline form in up to four polymorphic modifications. Therefore, the process of manufacturing the crystalline calcium salt of 5-methyl-(6S)-tetrahydrofolic acid has to be controlled very precisely. Additionally, the crystalline calcium salt of 5-methyl-(6S)-tetrahydrofolic acid of U.S. Pat. No. 6,441,168 B1 typically contains in the crystal lattice of all its polymorphic forms at least one but up to four equivalents of water per equivalent of 5-methyl-(6S)-tetrahydrofolic acid.

US 2016207925 A1 is claiming lyophilised, spray-dried or boiled down compositions comprising L-asparagine or L-arginine together with 5-methyl-(6S)-tetrahydrofolic acid. However the disclosed compositions are simple, non-stochiometric mixtures and exist in an amorphous state.

New crystal forms of a pharmaceutically useful compound offer an opportunity to improve the performance profile of a pharmaceutical and/or vitamin/medical food products. It widens the reservoir of materials a formulation scientist has available for designing new dosage forms with improved characteristics.

The technical problem underlying the present invention is the provision of a crystalline form comprising 5-methyl-(6S)-tetrahydrofolic acid which overcomes the drawbacks of the crystalline calcium salt of 5-methyl-(6S)-tetrahydrofolic acid known in the art.

Additionally, new crystalline forms often show desired different physical and/or biological characteristics, which may assist in the manufacture or formulation of the active compound, to the purity levels and uniformity required for regulatory approval.

For the sake of stability of tetrahydrofolates it is always the aim to provide a compound which has a low water absorption upon storage and which can be dried sufficiently during manufacturing. In addition, drug substances that do not absorb high amounts of water under ambient conditions are highly desired. Particularly desired are substances that do not change their water content when the ambient relative humidity changes because large changes of the water content due to change of the relative humidity of the environment make it more difficult to achieve a great precision with the respect to the dosage form.

The technical problem is solved by a crystalline salt comprising 5-methyl-(6S)-tetrahydrofolic acid and L-leucine ethyl ester wherein the molar ratio of 5-methyl-(6S)-tetrahydrofolic acid to L-leucine ethyl ester is from 1:0.3 to 1:3.0 (in mol/mol) and/or hydrates and/or solvates thereof.

The solid form of the present invention possesses improved pharmacological characteristics, thus offering enhanced possibilities to modulate and design improved drug products. Compared with the crystalline polymorphic forms of the calcium salt of 5-methyl-(6S)-tetrahydrofolic acid known in the art the water adsorption of the crystalline salt of 5-methyl-(6S)-tetrahydrofolic acid and L-leucine ethyl ester is significantly lower leading to substantially improved control over the target dosage form level in the drug product because the change of the amounts of adsorbed water under changing relative humidity conditions is significantly less pronounced.

Another advantageous aspect of the crystalline salt of 5-methyl-(6S)-tetrahydrofolic acid and L-leucine ethyl ester is that a high chemical and optical purity of 5-methyl-(6S)-tetrahydrofolic acid can be achieved in one single crystallization step.

It is advantageous when a drug has a high kinetic solubility when orally administered leading to an improved and faster bioavailability. Consequently, the medicament can function more readily.

5-methyl-(6S)-tetrahydrofolic acid is poorly soluble in water. The thermodynamically stable form of the calcium salt (Form III) is known to exhibit an aqueous solubility of about 2.5 mg/ml and the solubility of the metastable Form I is about 10 mg/ml at room temperature. Under certain pH conditions, in particular when the pH of the environments is lower than the equilibrium pH of a given salt, the salts can potentially disproportionate into free acid and as a consequence, the solubility decreases substantially. Therefore, thermodynamic solubilities of the claimed salts at about neutral to lower pH values are inaccessible due to slow salt disproportionation (formation of poorly soluble free acid). However, the bioavailability is dominated by kinetic effects. Administration of a solid form of a drug product is followed by dissolution and after the first dissolution step the drug is diluted by body fluids and distributed. Therefore the kinetic solubility is a key parameter that influences the bioavailability because the initially dissolved drug substance is readily diluted and transported. For the salt of 5-methyl-(6S)-tetrahydrofolic acid and L-leucine was surprisingly found that the kinetic solubility is improved by a factor of about two versus the known (metastable Form I) of the calcium salt. The difference in the kinetic solubility of the salt of the present invention to the thermodynamically stable form of the calcium salt (Form III) would presumably even be larger. Thus temporarily a much higher drug substance concentration can be achieved.

Additionally, the crystalline salt comprising 5-methyl-(6S)-tetrahydrofolic acid and L-leucine ethyl ester exists in its crystalline form in one clearly defined polymorphic modification. Therefore, the process of manufacturing the crystalline salt comprising 5-methyl-(6S)-tetrahydrofolic acid and L-leucine ethyl ester does not require very precise control of crystallisation conditions.

Preferably, the molar ratio of 5-methyl-(6S)-tetrahydrofolic acid to L-leucine ethyl ester is from 1:0.5 to 1:2.5 (in mol/mol).

Even more preferred, the molar ratio of 5-methyl-(6S)-tetrahydrofolic acid to L-leucine ethyl ester is from 1:0.75 to 1:1.25 (in mol/mol).

Preferably, the ratio of 5-methyl-(6S)-tetrahydrofolic acid to L-leucine ethyl ester is approximately 1:1 (in mol/mol) and/or hydrates and/or solvates thereof.

Preferably, the salt of the present invention is the crystalline salt of 5-methyl-(6S)-tetrahydrofolic acid and L-leucine ethyl ester and has a PXRD pattern with at least one characteristic peak (expressed in 2θ±0.2° 2θ (CuKα radiation)) selected from the following peaks located at 5.6, 6.9, 8.4, 12.9, 14.1, 17.5, 19.1, 21.2, 21.4 and 23.7.

Most preferred, the salt of the present invention is the crystalline salt of 5-methyl-(6S)-tetrahydrofolic acid and L-leucine ethyl ester and has a PXRD pattern with at least three characteristic peaks (expressed in 2θ±0.2° 2θ (CuKα radiation)) selected from the following peaks located at 5.6, 6.9, 8.4, 12.9, 14.1, 17.5, 19.1, 21.2, 21.4 and 23.7 and even more preferred, the salt of the present invention is the crystalline salt of 5-methyl-(6S)-tetrahydrofolic acid and L-leucine ethyl ester and has a PXRD pattern with characteristic peaks (expressed in 2θ±0.2° 2θ (CuKα radiation)) at 5.6, 6.9, 8.4, 12.9, 14.1, 17.5, 19.1, 21.2, 21.4 and 23.7.

Preferably, the salt of the present invention is the crystalline salt of 5-methyl-(6S)-tetrahydrofolic acid and L-leucine ethyl ester and has a PXRD pattern with at least one characteristic peak (expressed in 2θ±0.2° 2θ (CuKα radiation)) selected from the following peaks located at 5.6, 6.9, 8.4, 12.9, 13.8, 14.1, 15.0, 17.5, 18.2, 19.1, 19.7, 21.2, 21.4, 23.7, 26.1 and 27.6.

Most preferred, the salt of the present invention is the crystalline salt of 5-methyl-(6S)-tetrahydrofolic acid and L-leucine ethyl ester and has a PXRD pattern substantially as shown in FIG. 1.

Even more preferred, the aforementioned crystalline salts have at least 99 wt % or more chemical and/or stereoisomerical purity.

A further aspect of the present invention is a process for obtaining the crystalline salt comprising 5-methyl-(6S)-tetrahydrofolic acid L-leucine ethyl ester comprising the steps of:
 i) providing a mixture of 5-methyl-(6S)-tetrahydrofolic acid and L-leucine ethyl ester, optionally in a suitable solvent or a mixture of solvents
 ii) adding a base, optionally in a suitable solvent or a mixture of solvents, to dissolve the compounds;
 iii) heating the composition to at least 60° C. and optionally carrying out a clear filtration;
 iv) crystallizing and cooling the mixture to a temperature between 1° C. and 30° C., optionally adding more solvent or mixture of solvents; and
 v) isolating the obtained solid material and optionally drying the product.

Preferably, the molar ratio of 5-methyl-(6S)-tetrahydrofolic acid and L-leucine ethyl ester in step ii) is in the range of from 1:1 to 1:3.

More preferred, the solvent is water.

In step iii) and/or iv) seed crystals may be added.

Preferably L-leucine ethyl ester is used as L-leucine ethyl ester hydrochloride.

Also, a pharmaceutical composition, food additive and/or preparation comprising the crystalline salt comprising 5-methyl-(6S)-tetrahydrofolic acid and L-leucine ethyl ester and optionally one or more acceptable excipients is part of the present invention.

The pharmaceutical composition may be in the form of tablets, capsules, oral liquid preparations, powders, lyophilisates, granules, lozenges, reconstitutable powders, injectable or infusable solutions or suspensions or suppositories.

The pharmaceutical composition may further comprise at least one additional therapeutic agent and, preferably, is a pharmaceutical composition for oral, parenteral, intramuscular, intraspinal, intrathecal, periodontal, topical or rectal administration.

The use of the crystalline salt comprising 5-methyl-(6S)-tetrahydrofolic acid and L-leucine ethyl ester as constituent for the production of drugs and/or as a food additive is also covered by the present invention.

The crystalline salt comprising 5-methyl-(6S)-tetrahydrofolic acid and L-leucine ethyl ester can be used in the treatment in homocysteine-lowering, of anemia, neural tube defects, cardiovascular diseases, depression, cognitive impairment, Alzheimer's disease and osteoporosis and/or dietary management of low plasma and/or low red blood cell and/or low cerebrospinal fluid and/or low peripheral or central nervous system folate.

In summary, the profile of properties offered by the salt of 5-methyl-(6S)-tetrahydrofolic acid and L-leucine ethyl ester of the present invention is advantageous for use in medicaments or as food additive. Especially, the low change in water content in an environment from 20% to 75% relative humidity could not been foreseen by the skilled artisan.

Moreover, the kinetic solubility is larger, what could also not be foreseen by the skilled artisan.

EXAMPLES

Powder X-Ray Diffraction

Stoe Stadi P equipped with a Mythen1 K Detector; Cu-Kα1 radiation; standard measurement conditions: transmission; 40 kV and 40 mA tube power; curved Ge monochromator; 0.02° 2θ step size, 48 s step time, 1.5-50.5° 2θ scanning range; detector mode: step scan; 1° 2θ detector step; standard sample preparation: 10 to 20 mg sample was placed between two acetate foils; sample holder: Stoe transmission sample holder; the sample was rotated during the measurement. All sample preparation and measurement was done in an ambient air atmosphere.

TG-FTIR

Thermogravimetric measurements were carried out with a Netzsch Thermo-Microbalance TG 209 coupled to a Bruker FTIR Spectrometer Vector 22 (sample pans with a pinhole, $N_2$ atmosphere, heating rate 10 K/min).

DVS

DVS measurements are typically performed with an SPS11-100n "Sorptions Prüfsystem" from ProUmid (formerly "Projekt Messtechnik"), August-Nagel-Str. 23, 89079 Ulm (Germany).

Example 1: Preparation of the Salt of 5-Methyl-(6S)-Tetrahydrofolic Acid and L-Leucine Ethyl Ester without Seeding A mixture of 5.0 grams of 5-methyl-(6S)-tetrahydrofolic acid monohydrate ([6S]-diastereoisomer: 98.4%) and 13 ml of water was heated to about 80° C. under an argon atmosphere and 1.98 mL of an aqueous solution of sodium hydroxide (concentration 30% w/w) were added to form a solution. The solution was heated to about 80° C. and a solution of 4.20 grams of L-leucine ethyl ester hydrochloride in 13 mL of water was added. The heating bath was removed to allow the solution to cool to about 25° C. within about two hours. While cooling, the solution gradually changes into a concentrated suspension. The suspension was diluted with 15 ml of water and stirred at ambient temperature overnight. The reactor with the suspension was further cooled in an ice/water bath to about 1° C. within about half an hour. The suspension was then filtered with a fritted glass filter and the solid product was washed with five ml of cold water. The solid product was dried in a vacuum dryer at about 35° C./10 mbar overnight and examined by $^1$H-NMR and identified as 5-methyl-(6S)-tetrahydrofolic acid L-leucine ethyl ester 1:1 salt. Powder X-ray diffraction was carried out and a PXRD pattern of the crystalline L-leucine ethyl ester salt substantially as depicted in FIG. 1 was obtained. HPLC analysis showed that the purity was 98.7% area and the optical purity was increased to 99.7% [6S]-diastereoisomer.

Example 2: Preparation of the Salt of 5-methyl-(6S)-tetrahydrofolic Acid and L-leucine Ethyl Ester with Seeding A mixture of 5.0 grams of 5-methyl-(6S)-tetrahydrofolic acid monohydrate ([6S]-diastereoisomer: 98.4%) and 20 ml of water was heated to about 80° C. under a nitrogen atmosphere and 1.9 mL of an aqueous solution of sodium hydroxide (concentration 32% w/w) was added to form a solution. The solution was heated to about 61° C. and a solution of 4.20 grams of L-leucine ethyl ester hydrochloride in 20 mL of water was added. The heating bath was removed to allow the solution to cool to about 32° C. within about half an hour. While cooling, the solution was seeded at about 60° C. with a small amount of crystalline L-leucine ethyl ester salt that was prepared according to Example 1 and the solution gradually changed into a concentrated suspension. At about 49° C. the suspension was diluted with 12 ml of water. At about 32° C. the reactor with the suspension was further cooled in an ice/water bath and a clear solution formed. After stirring at ambient temperature overnight, 0.15 mL of a 37% (w/w) concentrated hydrochloric acid aqueous solution was added, followed by 0.5 mL hydrochloric acid in form of a 2.00 molar aqueous solution. At ambient temperature, the solution was seeded with a small amount of the salt of 5-methyl-(6S)-tetrahydrofolic acid and L-leucine ethyl ester that was prepared according to Example 1 and a weak suspension formed. The suspension was stirred at ambient temperature and an additional 0.35 mL of hydrochloric acid in form of a 2 molar aqueous solution was added. The suspension was cooled to about 2° C. and an additional 0.30 mL of hydrochloric acid in the form of a 2 molar aqueous solution was added. Stirring of the suspension was continued at about 2° C. for about 15 minutes and the suspension filtered with a fritted glass filter. The solid product was dried in a vacuum dryer at about 40° C./10 mbar and examined by $^1$H-NMR and identified as 5-methyl-(6S)-tetrahydrofolic acid L-leucine ethyl ester salt. Powder X-ray diffraction was carried out and a PXRD pattern of the L-leucine ethyl ester salt substantially as depicted in FIG. 1 was obtained; however, the PXRD pattern revealed that the sample contained a small amount of NaCl. HPLC analysis shows that the purity is 98.39% area and the optical purity was increased to 99.7% [6S]-diastereoisomer.

Example 3: Washing the Salt of 5-methyl-(6S)-tetrahydrofolic Acid and L-leucine Ethyl Ester About 420 mg of the solid material obtained in Example 2 was weighed into a filter centrifuge device and 2.0 mL of water is added followed by centrifugation under ambient conditions. This wash step is repeated twice more using 0.5 mL of water. The wet filter cake is then transferred to a fritted glass filter and air dried by drawing ambient air (about 22° C./about 21% r.h.) through the glass filter for about 10 minutes. The dried material was examined by $^1$H-NMR and identified as a 5-methyl-(6S)-tetrahydrofolic acid L-leucine ethyl ester 1:1 salt. TG-FTIR analysis showed that the sample contained only about 0.7% of water. Powder X-ray diffraction was carried out and a PXRD pattern of the L-leucine ethyl ester salt substantially as depicted in FIG. 1 was obtained which exhibits peaks at 2-theta angles as listed in Table 1.

TABLE 1

2-theta angles, d-spacings and qualitative intensities for 5-methyl-(6S)-tetrahydrofolic acid L-leucine ethyl ester salt according to example 3.

| angle °2Θ | d-spacing [Å] | qualitative intensity |
|---|---|---|
| 2.8 | 31.7 | m |
| 5.6 | 15.7 | s |
| 6.9 | 12.9 | vs |
| 8.4 | 10.5 | s |
| 10.6 | 8.4 | w |
| 11.3 | 7.8 | w |
| 12.9 | 6.9 | s |
| 13.8 | 6.4 | m |
| 14.1 | 6.3 | s |
| 14.5 | 6.1 | m |
| 15.0 | 5.90 | m |
| 15.5 | 5.70 | w |
| 15.8 | 5.61 | m |
| 16.4 | 5.41 | m |
| 17.0 | 5.22 | m |
| 17.5 | 5.07 | s |
| 18.2 | 4.88 | s |
| 18.6 | 4.78 | m |
| 19.1 | 4.64 | s |
| 19.7 | 4.50 | m |
| 20.2 | 4.40 | w |
| 20.6 | 4.32 | w |
| 20.9 | 4.25 | w |
| 21.2 | 4.18 | s |
| 21.4 | 4.15 | s |
| 22.3 | 3.98 | m |
| 22.6 | 3.93 | m |
| 23.0 | 3.86 | w |
| 23.4 | 3.80 | w |
| 23.7 | 3.75 | s |
| 24.3 | 3.65 | w |

TABLE 1-continued 2-theta angles, d-spacings and qualitative intensities
for 5-methyl-(6S)-tetrahydrofolic acid L-leucine
ethyl ester salt according to example 3.

| angle °2Θ | d-spacing [Å] | qualitative intensity |
|---|---|---|
| 24.7 | 3.61 | w |
| 25.0 | 3.56 | w |
| 25.2 | 3.53 | w |
| 25.5 | 3.49 | w |
| 26.1 | 3.41 | m |
| 26.7 | 3.34 | w |
| 27.1 | 3.29 | w |
| 27.6 | 3.23 | m |
| 28.0 | 3.18 | w |
| 28.3 | 3.15 | w |
| 28.6 | 3.12 | w |

Vs = very strong, s = strong, m = medium, w = weak, and vw = very weak in intensity.
It should be noted that intensity values can vary substantially due to preferred orientation effects.

Example 4: Hygroscopicity and Water Content (DVS Experiments)

The water content of a sample of 5-methyl-(6S)-tetrahydrofolic acid calcium salt was measured and found to be 12.4%. TG-FTIR analysis of a sample of 5-methyl-(6S)-tetrahydrofolic acid L-leucine ethyl ester salt according to Example 3 showed that the sample contained only about 0.7% of water. A sample of 5-methyl-(6S)-tetrahydrofolic acid calcium salt and a sample of 5-methyl-(6S)-tetrahydrofolic acid L-leucine ethyl ester salt according to Example 3 (about 20 mg each) were examined by dynamic water vapor sorption analysis (DVS) within the relative humidity range from 0 to 75% r.h. DVS measurements were performed as follows: The sample was placed on an aluminum holder on top of a microbalance and allowed to equilibrate at 50% RH before starting the pre-defined humidity program:
   (1) two hours kept at 50% constant relative humidity (RH) then
   (2) reduced to 0% RH at a rate of 5% per hour
   (3) maintained RH at 0% for five hours
   (4) raised RH to 75% at a rate of 5% per hour
   (5) maintained RH at 75% for five hours
   (6) reduced to 0% RH at a rate of 5% per hour
   (7) maintained RH at 0% for five hours
   (8) raised RH to 75% at a rate of 5% per hour
   (9) reduced to 50% RH at a rate of 5% per hour
   (10) maintained RH at 50% for about one hour Comparing the result for 5-methyl-(6S)-tetrahydrofolic acid L-leucine ethyl ester salt with the result for the calcium salt shows that the water content of 5-methyl-(6S)-tetrahydrofolic acid L-leucine ethyl ester salt changes about 2.6% within the tested range, while the water content for the calcium salt changes by about 7.4%. The results are illustrated in FIG. 2.

Example 5: Kinetic Solubility of the Crystalline Salt of 5-methyl-(6S)-tetrahydrofolic Acid and L-leucine Ethyl Ester 43.1 mg of the anhydrous form of the crystalline 5-methyl-(6S)-tetrahydrofolic acid L-leucine ethyl ester salt according to Example 3 were weighed into a 7 mL glass vial with a screw cap. 2.00 mL of purified/de-ionized water (for instance water for chromatography) was added to the solid using an adjustable volumetric pipette. The mixture was vigorously agitated at room temperature for one minute. After one minute a turbid solution was observed suggesting that most of the sample was dissolved. The solution was filtered by centrifugal filtration and 1.50 mL of the aqueous solution was transferred into a tared glass vial (about 10 mL volume). The water was evaporated in an air dryer at 40° C. for about 15 hours, then at 50° C. for about eight hours, subsequently drying was completed at 50° C. under vacuum (10 to 20 mbar) for about 13 hours. The solubility was determined by gravimetric evaluation of the solid residue. The solubility was 15.1 mg of 5-methyl-(6S)-tetrahydrofolic acid per mL.

Reference Example 1: Kinetic Solubility of the Calcium Salt of 5-methyl-(6S)-tetrahydrofolic Acid 42.5 mg of the anhydrous form of the crystalline 5-methyl-(6S)-tetrahydrofolic acid calcium salt were weighed into a 7 mL glass vial with a screw cap. 2.00 mL of purified/de-ionized water (for instance water for chromatography) was added to the solid using an adjustable volumetric pipette. The mixture was vigorously agitated at room temperature for one minute. After one minute a suspension was observed. The suspension was filtered by centrifugal filtration and 1.50 mL of the aqueous solution was transferred into a tared glass vial (about 10 mL volume). The water was evaporated in an air dryer at 40° C. for about 15 hours, then at 50° C. for about eight hours, subsequently drying was completed at 50° C. under vacuum (10 to 20 mbar) for about 13 hours. The solubility was determined by gravimetric evaluation of the solid residue. The solubility was 9.0 mg of 5-methyl-(6S)-tetrahydrofolic acid per mL.

Figure 1:
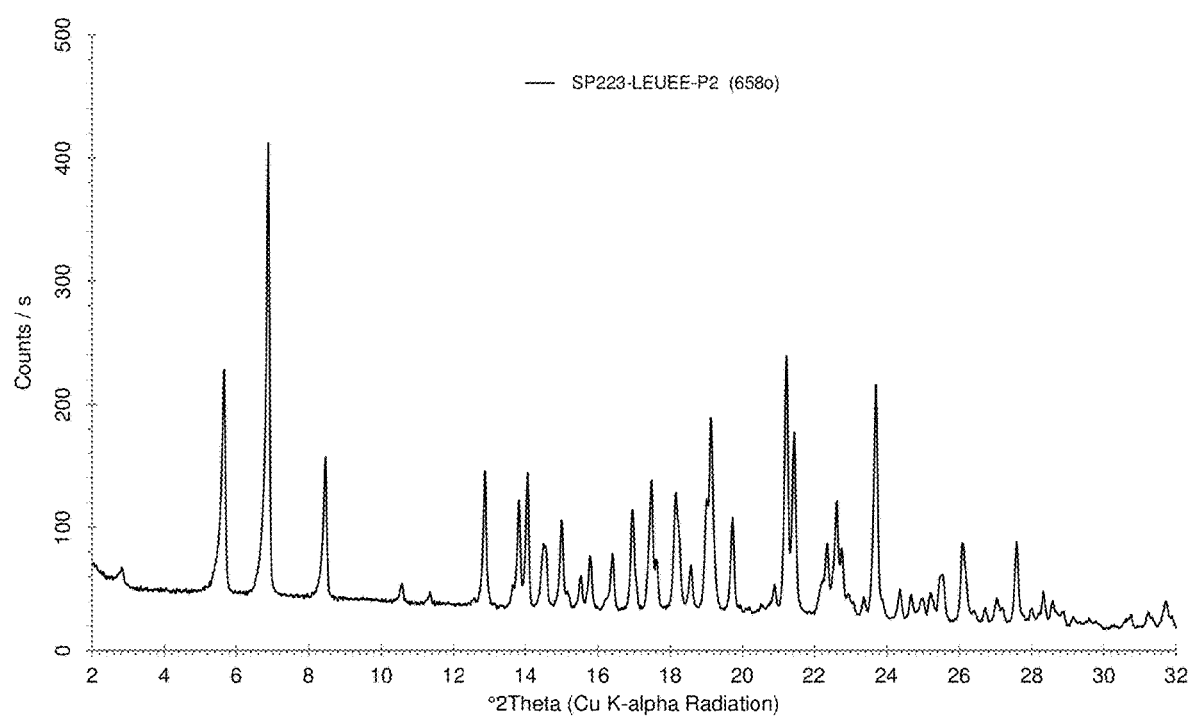
FIG. 1 is an X-ray diffraction pattern.
Figure 2:
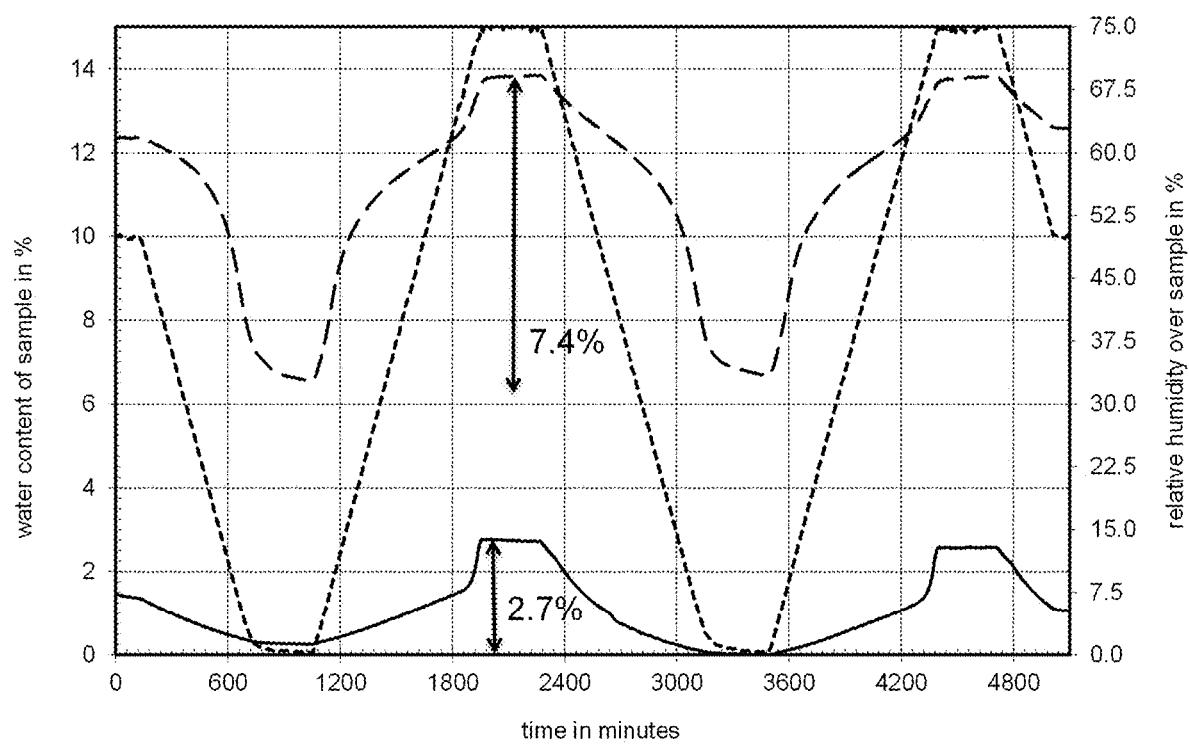
FIG. 2 is a graph.

The invention claimed is:

1. A crystalline salt comprising 5-methyl-(6S)-tetrahydrofolic acid and L-leucine ethyl ester, wherein the molar ratio of 5-methyl-(6S)-tetrahydrofolic acid to L-leucine ethyl ester is 1:0.75 to 1:1.25 (in mol/mol) or a hydrate or solvate thereof.

2. The crystalline salt of claim 1, wherein the salt is the salt of 5-methyl-(6S)-tetrahydrofolic acid and L-leucine ethyl ester and has a PXRD pattern with at least three characteristic peaks (expressed in 2θ±0.2° 2θ (CuKα radiation)) selected from the following peaks located at 5.6, 6.9, 8.4, 12.9, 14.1, 17.5, 19.1, 21.2, 21.4 and 23.7.

3. The crystalline salt of claim 1 having at least 99 wt % or more chemical and/or stereoisomerical purity.

4. A process for obtaining the crystalline salt comprising 5-methyl-(6S)-tetrahydrofolic acid and L-leucine ethyl ester according to claim 1 comprising the steps of:
   i) providing a mixture of 5-methyl-(6S)-tetrahydrofolic acid and L-leucine ethyl ester, in water as a solvent;
   ii) adding sodium as a base, optionally in water as a solvent, to dissolve the compounds;
   iii) heating the composition to at least 60° C. and optionally carrying out a clear filtration;
   iv) crystallizing and cooling the mixture to a temperature between 1° C. and 30° C., optionally adding more water as a solvent; and
   v) isolating the obtained solid material and optionally drying the product.

5. The process of claim 4, wherein the molar ratio of 5-methyl-(6S)-tetrahydrofolic acid and L-leucine ethyl ester in step i) is 1:0.75 to 1:1.25 (in mol/mol).

6. The process of claim 4, wherein in step iii) and/or iv) seed crystals are added.

7. The process of claim 4, wherein the L-leucine ethyl ester is used as L-leucine ethyl ester hydrochloride.

8. A pharmaceutical composition, food additive and/or preparation comprising the crystalline salt comprising 5-methyl-(6S)-tetrahydrofolic acid and L-leucine ethyl ester according to claim 1 and optionally one or more acceptable excipients.

9. The pharmaceutical composition according to claim 8, which has been prepared from the crystalline salt comprising 5-methyl-(6S)-tetrahydrofolic acid and L-leucine ethyl ester, and which is in the form of a product selected from the group consisting of tablets, capsules, oral liquid preparations, powders, lyophilisates, granules, lozenges, reconstitutable powders, injectable solutions, infusable solutions, suspensions and suppositories.

10. The pharmaceutical composition according to claim 8 further comprising at least one additional therapeutic agent.

11. The pharmaceutical composition according to claim 8, which is a pharmaceutical composition that is suitable for oral, parenteral, intramuscular, intraspinal, intrathecal, periodontal, topical or rectal administration.

12. A method which comprises incorporating the crystalline salt comprising 5-methyl-(6S)-tetrahydrofolic acid and L-leucine ethyl ester according to claim 1 as constituent and/or additive in the production of a drug and/or food.

13. A method of treatment by homocysteine-lowering, of anemia, a neural tube defect, a cardiovascular disease, depression, cognitive impairment, Alzheimer's disease, osteoporosis, or dietary management of low plasma or low red blood cell or low cerebrospinal fluid or low peripheral or central nervous system folate, comprising administering to a subject in need thereof an effective amount of the crystalline salt comprising 5-methyl-(6S)-tetrahydrofolic acid and L-leucine ethyl ester according to claim 1.

* * * * *